United States Patent
Doyle, III et al.

(10) Patent No.: US 11,197,955 B2
(45) Date of Patent: Dec. 14, 2021

(54) MODEL-BASED PERSONALIZATION SCHEME OF AN ARTIFICIAL PANCREAS FOR TYPE I DIABETES APPLICATIONS

(71) Applicant: The Regents of the University of California, Oakland, CA (US)

(72) Inventors: Francis J. Doyle, III, Santa Barbara, CA (US); Eyal Dassau, Goleta, CA (US); Dale E. Seborg, Santa Barbara, CA (US); Joon Bok Lee, Santa Barbara, CA (US)

(73) Assignee: The Regents of the University of California, Oakland, CA (US)

( * ) Notice: Subject to any disclaimer, the term of this patent is extended or adjusted under 35 U.S.C. 154(b) by 250 days.

(21) Appl. No.: 16/574,076

(22) Filed: Sep. 17, 2019

(65) Prior Publication Data

US 2020/0078516 A1    Mar. 12, 2020

Related U.S. Application Data

(63) Continuation of application No. 14/792,524, filed on Jul. 6, 2015, now Pat. No. 10,413,664.

(51) Int. Cl.
*A61M 5/172*    (2006.01)
*A61F 2/02*    (2006.01)

(52) U.S. Cl.
CPC .......... *A61M 5/1723* (2013.01); *A61F 2/022* (2013.01); *A61M 2005/1726* (2013.01); *A61M 2205/52* (2013.01)

(58) Field of Classification Search
CPC ............ A61M 5/1723; A61M 5/14244; G16H 20/17; G16H 50/50; A61B 5/14532; A61B 5/4839; A61K 38/28
See application file for complete search history.

(56) References Cited

U.S. PATENT DOCUMENTS

2010/0228110 A1\*    9/2010    Tsoukalis ............... A61B 5/685
                                                                        600/347
2012/0123234 A1\*    5/2012    Atlas ..................... G16H 50/50
                                                                        600/365

\* cited by examiner

*Primary Examiner* — Manuel A Mendez
(74) *Attorney, Agent, or Firm* — Richard Aron Osman (57) ABSTRACT

A model-based control scheme consisting of either a proportional-integral-derivative (IMC-PID) controller or a model predictive controller (MPC), with an insulin feedback (IFB) scheme personalized based on a priori subject characteristics and comprising a lower order control-relevant model to obtain PID or MPC controller for artificial pancreas (AP) applications.

15 Claims, 3 Drawing Sheets

MODEL-BASED PERSONALIZATION SCHEME OF AN ARTIFICIAL PANCREAS FOR TYPE I DIABETES APPLICATIONS

This invention was made with government support under Grant Numbers DP3DK094331-01 and ROIDK085628 awarded by the National Institutes of Health (NIH). The government has certain rights in the invention.

INTRODUCTION

Nearly 16,000 new cases of Type 1 diabetes mellitus are diagnosed annually among people younger than 20 years of age in the United States alone [1]. Without treatment, these individuals suffer effects of unnaturally high blood glucose concentrations (called "hyperglycemia", defined as having a blood glucose concentration greater than 180 mg/dl [2]), leading to diabetic ketoacidosis and long-term complications such as cardiovascular disease, kidney failure, blindness, and death [3]. Manual administration of exogenous insulin to treat T1DM requires multiple exacting calculations of blood glucose concentrations and carbohydrate ingestion daily, as even a slight overdose may cause immediate life-threatening consequences of low blood glucose concentrations (called "hypoglycemia" and generally defined as having a blood glucose concentration lower than 70 mg/dl [2]), including trembling, weakness, difficulty speaking, convulsion, unconsciousness, and death [3]. Due to these and other complications, the average life expectancy of individuals with type 1 diabetes continues to lag at least a decade behind that of the overall population [4].

The key component in a successful artificial pancreas (AP) system designed to help these people is the control algorithm that can automatically direct the delivery of insulin with or without a pre meal bolus. A closed-loop system combines a subcutaneous continuous glucose monitor (CGM) and continuous subcutaneous insulin injections (CSII) pump to deliver insulin.

There are two main approaches for control design of AP: (a) proportional-integral-derivative (PID) controllers [5-7], and (b) model predictive control (MPC) controllers [8-10]. There are other approaches that are also being evaluated, such as fuzzy logic [11] and artificial neural networks [12]. The use of an internal model-based PID controller (IMC-PID) and MPC for AP systems is disclosed here. IMC based approach for tuning PID controllers have an advantage in that it only requires a single tuning parameter to modify controller performance [13]. Among different control-relevant models that have been made available in varying complexities, a discrete third order model with a priori subject information proposed by Van Heusden et al. [14] can be used to design a PID and an MPC controller based on an identical linear model. A subject's basal insulin injection characteristic is incorporated in addition to the total daily insulin (TDI) clinical parameter used by Van Heusden et al. to further attune the controller action in cases of model and patient mismatch.

The disclosed controller also incorporates an insulin feedback scheme (IFB) which accelerates the apparent insulin pharmacokinetic profile. PID controllers that incorporate this scheme can exhibit improved performance, as shown in both model simulations [15] and a clinical trial [16].

Below are described (i) the control challenges for glucose regulations in subjects with T1DM, (ii) the development of the IMC-PID controller, incorporation of the additional personalization factor, and adoption of the IFB, (iii) incorporation of the additional personalization factor in the MPC controller (iv) implementation of variations of this controller in in silico trials, and (v) a discussion of the results.

SUMMARY OF THE INVENTION

The key component in a successful artificial pancreas system designed to maintain the blood glucose concentrations of people with type 1 diabetes mellitus within the euglycemic zone (80-140 mg/dl) is the control algorithm, which automatically directs the delivery of insulin to be administered to a subject with type 1 diabetes. The controller must meet a variety of challenges, such as the inherent long time delays between subcutaneous sensing, subcutaneous pump action, and the body's insulin-blood glucose dynamics, among others. The performance of any algorithm is limited by the development of a reliable model from which to base the controller design—controllers based on irrelevant models may not deal with the particular control challenges inherent in the artificial pancreas applications successfully, inducing hypoglycemic risk within the subjects. The invention combines an internal model control based design of a proportional-integral-derivative controller with individual gain personalization based on each subject's clinical characteristics. The invention uses a discrete model with a priori subject information; in particular embodiments the personalized controller is based on a lower order model, such as a $3^{rd}$ order model, but $1^{st}$, $2^{nd}$, $4^{th}$, $5^{th}$ or other lower order model may be used, and preferred lower dimensional models are s order or lower. The subject's basal insulin is incorporated into the lower order model to further personalize the controller's aggressiveness and take into account the wide variations in insulin sensitivity throughout the population. This personalization allows the controller to be appropriately aggressive in cases where the subject is insensitive to insulin and requires a large basal amount to maintain euglycemia, while preventing hypoglycemic risk by bringing down the controller's aggressiveness in cases where the subject requires a low basal amount to maintain normal blood glucose levels.

In one aspect the invention provides an internal model-based proportional-integral-derivative (IMC-PID) controller with an insulin feedback (IFB) scheme personalized based on a priori subject characteristics and comprising a lower order control-relevant model to obtain PID controller parameters through an IMC based approach adapted for artificial pancreas (AP) applications.

In another aspect the invention provides a model-predictive controller (MPC) personalized based on a priori subject characteristics and comprising a lower order control-relevant model adapted and configured for artificial pancreas (AP) applications.

In another aspect the invention provides an internal model-based proportional-integral-derivative (IMC-PID) controller adapted for an artificial pancreas (AP) system which controller requires only a single tuning parameter to modify controller performance and comprises a discrete lower order model with a priori subject information as design criteria, wherein a subject's basal insulin injection characteristic is incorporated, in addition to the total daily insulin (TDI) clinical parameter to further attune the controller's action in cases of model and patient mismatch, and an insulin feedback scheme (IFB), which accelerates the apparent insulin pharmacokinetic profile.

In another aspect the invention provides a model-predictive controller (MPC) adapted and configured for an artificial pancreas (AP) system which controller comprises a discrete lower order model with a priori subject information as design criteria, wherein a subject's basal insulin injection characteristic is incorporated, in addition to the total daily insulin (TDI) clinical parameter to further attune the controller's action in cases of model and patient mismatch In another aspect the invention provides a controller for an artificial pancreas (AP) system adapted to maintain blood glucose concentrations of people with type 1 diabetes mellitus within the euglycemic zone (80-140 mg/dl) comprising a control algorithm, and which automatically directs the delivery of insulin to be administered to a subject with type 1 diabetes, comprising an internal model control (IMC) based design of a proportional-integral-derivative (PID) controller with individual gain personalization based on each subject's clinical characteristics, using a lower order discrete model with a priori subject information, wherein the subject's basal insulin is incorporated into the lower order model to further personalize the controller's aggressiveness and take into account variations in insulin sensitivity, wherein the personalization allows the controller to be aggressive in cases where the subject is insensitive to insulin and requires a large basal amount to maintain euglycemia, while preventing hypoglycemic risk by reducing the controller's aggressiveness in cases where the subject requires a low basal amount to maintain normal blood glucose levels.

In another aspect the invention provides a controller for an artificial pancreas (AP) system adapted to maintain blood glucose concentrations of people with type 1 diabetes mellitus within a setpoint or predefine glycemic zone such as the euglycemic zone (80-140 mg/dl) comprising a control algorithm, and which automatically directs the delivery of insulin to be administered to a subject with type 1 diabetes, comprising a model-predictive controller (MPC) with individual gain personalization based on each subject's clinical characteristics, using a lower order discrete model with a priori subject information, wherein the subject's basal insulin is incorporated into the lower order model to further personalize the controller's aggressiveness and take into account variations in insulin sensitivity, wherein the personalization allows the controller to be aggressive in cases where the subject is insensitive to insulin and requires a large basal amount to maintain euglycemia, while preventing hypoglycemic risk by reducing the controller's aggressiveness in cases where the subject requires a low basal amount to maintain normal blood glucose levels.

The invention also provides corresponding algorithms for programming the subject controllers to effectively implement the disclosed control steps.

The invention also provides an artificial pancreas system or subsystem comprising a subject controller, which may comprise for example, the controller and a pump.

The invention also provides a model-based personalization scheme of an artificial pancreas (AP) for Type 1 diabetes applications comprising a control algorithm which controls a subject controller.

The invention also provides a method comprising directing insulin delivery using a subject controller, and optionally delivering the insulin.

The invention includes controllers, algorithms and insulin directing systems essentially as described herein, and includes all combinations of the recited particular embodiments. All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

DESCRIPTION OF PARTICULAR EMBODIMENTS OF THE INVENTION

Control Specifications

Controllers are assessed as a part of an AP system that utilizes noise-free and noise-included blood glucose measurements and continuous subcutaneous insulin injections. The system is incorporated as a part of a ten subject study using the Food and Drug Administration (FDA) accepted University of Virginia and Padova (UVA/Padova) metabolic simulator [17]. The control sampling period are set to 5 minutes. An unannounced meal is used to challenge the system without prior insulin bolus (feedforward action) to counteract the meal. The control system is evaluated by its performance in 1) minimizing the postprandial blood glucose concentration peak;
2) maximizing the time the subject's blood glucose concentration remains within the euglycemic zone (approximately 80-140 mg/dl) [18]; and
3) minimizing the time the subject's blood glucose concentration spends below the target zone (approximately 70-180 mg/dl) [18].

A controller that is implemented in this manner must meet a variety of challenges. The use of subcutaneous monitoring, while unobtrusive compared to intravenous measurements, adds a measurement delay of approximately 12 minutes [19]. The use of subcutaneous insulin pumps also adds an additional actuation delay of up to one hour before the injected insulin affects glucose concentration [20]. Insulin cannot be delivered in negative values. Consequently, avoidance of excess insulin delivery is imperative.

Model-Based Subject Specific Proportional Integral Derivative Control Algorithm Development Development of a model that is used for control purposes must be optimized for different objectives than the traditional goal of modeling that is, rather than focusing on deriving an accurate prediction of future glucose values, the model should rather be designed with the specific control goal in mind [14]. In our previous work, we proposed a discrete 3rd order control-relevant model $M_r$ defined as $$M_r(q) = \frac{Kq^{-3}}{(1-0.98q^{-1})(1-0.965q^{-1})^2} \qquad (1)$$

where $q^{-1}$ is the backward shift operator as described in [14], the units of insulin is expressed as (pmol/min), and blood glucose concentration is expressed as (mg/dl). For further details on the development of this model, the reader is referred to [14].

K can be personalized using a priori subject parameters as $$K = K_f c S F_b \qquad (2)$$

where $K_i$ is an individualized gain based on the correction factor calculated as $$K_i = K_x/\text{TDI} \tag{3}$$

$$1600 \leq K_x \leq 2400 \tag{4}$$

using the range of rules for calculating correction factor as shown in [18]. TDI represents the subject's total daily insulin requirement, an easily available clinical parameter for any subject with a history of type 1 diabetes. c is a factor to maintain consistency in units as $$C = \frac{1}{\frac{1U}{6.64\,\text{h}} * \frac{6000\,\text{pm}}{1U} * \frac{1\,\text{h}}{60\,\text{min}}} \tag{5}$$

with the average clearance time for 99% of 1 U of Humalog insulin analog to leave the system represented as 6.64 h (1 h half time in an average adult [21]) and conversion for 1 U of insulin applied as 6000 pm as per the standard clinical definition. $SF_b$ is a scaling factor based on the actual value of the subject's basal profile, another easily available clinical parameter, versus what is recommended as the standard starting basal quantity calculated from their TDI prior to further adjustments, as follows $$SF_b = b_{calc}/(b) \tag{6}$$

$$b_{calc}(\text{U/h}) = (K_y \text{TDI})/24 \tag{7}$$

$$0.4 \leq K_y \leq 0.6 \tag{8}$$

Here, b is the subject's actual nominal basal in U/h, and $b_{calc}$ is the recommended calculation for a subject with T1DM's initial basal rate prior to fine-tuning, with the factor in the formula for the calculation varying between 0.4 and 0.6 depending on the subject's fitness, age, and other characteristics. Basal insulin profile of a subject with T1DM is a standard part of the subject's daily injection regimen, and is designed to maintain the subject at euglycemia absent meal disturbances [18]. Thus, this unitless scaling factor can attenuate the control signal based on how much more or less insulin the subject actually requires to maintain open-loop glucose concentration compared to the standard as calculated by the subject TDI, thus providing a measure of insulin sensitivity greater or less than standard.

The discrete model as shown in (1) can be transformed to continuous domain using a bilinear transform approximation as The discrete model as shown in (1) can be transformed to continuous domain using a bilinear transform approximation as $$q = e^{sT_s} \sim \frac{1 + s\frac{T_s}{2}}{1 - s\frac{T_s}{2}} \tag{9}$$

where $T_s$ is the sampling time of the discretized model at 5 minutes. The result of this discretization gives $M_{r1}(s)$ a $$M_{r1}(s) = \frac{Ke^{-15s}(-2s+1)^3}{(247s+1)(140s+1)^2}. \tag{10}$$

(8) can be converted into a second order plus time delay model through Skogestad's half rule [22]. This results in a second order plus time delay model of the form $$\tilde{G}(s) = \frac{Ke^{-\theta s}}{(\tau_1 s + 1)(\tau_2 s + 1)}. \tag{11}$$

From the original model (8), one can find the new $\theta$, $\tau_1$ and $\Sigma_2$ as $$\theta = 140/2 + 15 + 3 \cdot 2 + 5/2 = 91.5 \tag{12}$$

$$\tau_1 = 247 \tag{13}$$

$$\tau_2 = 140 + 140/2 = 210 \tag{14}$$

These calculations give the final model as $$M_{r2}(s) = \frac{Ke^{-93.5s}}{(247s+1)(210s+1)}. \tag{15}$$

Given a reasonably accurate dynamic model of the process, a method of controller design based on the process model is an approach that holds many advantages. The IMC method allows for model uncertainty and gives the user the capability to modify the tradeoffs of increased robustness versus better performance from tuning just one parameter.

The second order plus time delay model from (15) can be factored with a first order Taylor series approximation of the time delay as $$M_{r2}(s) = M_{r2+}(s)M_{r2-}(s) \tag{16}$$

$$M_{r2+}(s) = 1 - \theta s \tag{17}$$

$$M_{r2-}(s) = \frac{K}{(\tau_1 s + 1)(\tau_2 s + 1)}. \tag{18}$$

The IMC method for PID controller tuning relations calls for a low pass filter with a gain of 1 and a tuning parameter $\tau_c$, leading to the calculations of the three PID controller parameters $K_c$, $\tau_I$ and $\tau_D$ as [23]

$$K_c K = \frac{\tau_1 + \tau_2}{\tau_c + \theta} \tag{19}$$

$$\tau_I = \tau_1 + \tau_2 \tag{20}$$

$$\tau_D = \frac{\tau_1 \tau_2}{\tau_1 + \tau_2} \tag{21}$$

Consequently, the PID controller settings can be simplified as $$K_{c1f} = -\frac{458}{\tau_c + 93.5} \cdot \frac{1}{\frac{K_x}{\text{TDI}} \cdot \frac{1}{\frac{1}{6.64} * 6000 * \frac{1}{60}} \cdot \frac{K_y * \text{TDI}}{24}} \tag{22}$$

$$= -\frac{298}{(\tau_c + 93.5)K_x K_y} b$$

$$\tau_I = 458 \quad (23)$$

$$\tau_D = 113 \quad (24)$$

with the choice of either of each rule's extremes to be determined and the specific value of $\tau_c$ (min) left as a tuning parameter. As a result of the additional personalization based on the subject's basal profile, the numerical value of the subject TDI is canceled from the controller, leaving the final form of the gain to only include the subject's current basal levels as their target (the units are still maintained).

The control signal as a result of the application of these parameters in the standard parallel form of the PID controller is added on the subject's basal to signal the final suggested insulin delivery $ID_{PID}$ to the insulin pump. This insulin signal can then be further attenuated by the use of IFB [15], which takes into account the amount of insulin previously delivered, accelerating the apparent insulin pharmacokinetics as $$\hat{I}_p(n) = K_0 ID(n-1) + K_1 \hat{I}_p(n-1) - K_2 \hat{I}_p(n-2) \quad (25)$$

$$ID(n) = (1+\gamma) ID_{PID}(n) - \gamma \hat{I}_p(n-1) \quad (26)$$

Here, n denotes the most recent time value, ID(n) is the final insulin delivery profile, and $I_p(n)$ is a real time estimate of insulin concentration. $K_1$, $K_2$, and $\gamma$ are constants each reported as 1.966308, 0.966584, and 0.5, with $K_0$ given as $$K_0 =: 1 - K_1 + K_2. \quad (27)$$

For more details on the development of this IFB scheme, the reader is directed to [15] and [16].

Model-Based Subject Specific Model Predictive Control Algorithm Development

The model as described in (18) can also be used to derive a model predictive controller; that is, a model predictive controller that explicitly employs a model of the process to be controlled when optimizing the input.

An example MPC algorithm employs a linear time-invariant $M_r$ defined as $$M_r(q) = \frac{Kq^{-3}}{(1 - 0.98q^{-1})(1 - 0.965q^{-1})^2} \quad (28)$$

where $q^{-1}$ is the backward shift operator as described in [14], the units of insulin is expressed as (pmol/min), and blood glucose concentration is expressed as (mg/dl). K can be personalized using a priori subject parameters as $$K = K_i c SF_b \quad (29)$$

where $K_i$ is an individualized gain based on the correction factor calculated as $$K_i = K_x / TDI \quad (30)$$

$$1600 \leq K_x \leq 2400 \quad (31)$$

using the range of rules for calculating correction factor as shown in [18]. TDI represents the subject's total daily insulin requirement, an easily available clinical parameter for any subject with a history of type 1 diabetes. c is a factor to maintain consistency in units as $$C = \frac{1}{\frac{1U}{6.64\,h} * \frac{6000\,pm}{1U} * \frac{1\,h}{60\,min}} \quad (32)$$

with the average clearance time for 99% of 1 U of Humalog insulin analog to leave the system represented as 6.64 h (1 h half time in an average adult [21]) and conversion for 1 U of insulin applied as 6000 pm as per the standard clinical definition. $SF_b$ is a scaling factor based on the actual value of the subject's basal profile, another easily available clinical parameter, versus what is recommended as the standard starting basal quantity calculated from their TDI prior to further adjustments, as follows $$SF_b = b_{calc}/(b) \quad (33)$$

$$b_{calc}(U/h) = (K_y TDI)/24 \quad (34)$$

$$0.4 \leq K_y \leq 0.6 \quad (35)$$

Here, b is the subject's actual nominal basal in U/h, and $b_{calc}$ is the recommended calculation for a subject with T1DM's initial basal rate prior to fine-tuning, with the factor in the formula for the calculation varying between 0.4 and 0.6 depending on the subject's fitness, age, and other characteristics. Basal insulin profile of a subject with T1DM is a standard part of the subject's daily injection regimen, and is designed to maintain the subject at euglycemia absent meal disturbances [18]. Thus, this unitless scaling factor can attenuate the control signal based on how much more or less insulin the subject actually requires to maintain open-loop glucose concentration compared to the standard as calculated by the subject TDI, thus providing a measure of insulin sensitivity greater or less than standard. Next, let $$b_1 = p_1 + 2p_2 = 2.91$$

$$b_2 = -2p_1 p_2 - p_2^2 = -2.8226$$

$$b_3 = p_1 p_2^2 = 0.9126. \quad (31)$$

For use in MPC the linear time-invariant system described by transfer function is re-written in state-space form as $$x(k+1) = Ax(k) + BI'(k)$$

$$G'(k) = Cx(k) \quad (32)$$

with system state $$x(k) = \begin{bmatrix} x_1(k) \\ x_2(k) \\ x_3(k) \end{bmatrix} \quad (33)$$

and parameter matrices $$A = \begin{bmatrix} b_1 & b_2 & b_3 \\ 1 & 0 & 0 \\ 0 & 1 & 0 \end{bmatrix} \quad (34)$$

$$B = \begin{bmatrix} K \\ 0 \\ 0 \end{bmatrix}$$

$$C = \begin{bmatrix} 0 & 0 & 1 \end{bmatrix}.$$

This formulation is explicitly employed by the MPC to predict the evolution of future glucose values, and optimize the insulin delivery based on a specific cost objective that penalizes glycemic/insulin baseline deviations.

To emphasize, the same model can be used in the design and development of both MPC and PID controllers. While an MPC utilizes the model directly, the IMC approach of the design of a PID controller gives exact, analytical expressions of the three constants that define PID controller settings (proportional, integral, and derivative time constants) based on the core model [23]. Thus, this method shows what the parameters of an IMC PID controller should be if it were an exact inversion of the model that describes the target process. In fact, under appropriate tuning, a one-step MPC controller can be realized to be identical to an IMC PID controller [13]. Fundamentally, IMC PID and MPC designs based on the same model are mathematically similar, and their performances will also be closely linked [13]

Results

The performance of the designed PID controller is tested in silico within the FDA accepted UVA/Padova metabolic simulator [17]. The improvement in the performance of the designed PID controller can be directly related to the performance improvements of the designed MPC controller, as the designed MPC controller is derived from an identical model with the same personalization scheme. The simulator contains ten subject models with various time-invariant clinical characteristics that have a large intersubject variability. The simulator also has the capability of providing an optimal bolus injection when given the meal size for each subject based on the subject's basal rate and insulin to carbohydrate ratio (I:C), a clinical parameter that signifies how many grams of carbohydrates are compensated for that specific patient for a unit of insulin.

Optimal regulation, in the context of the disclosed AP, is defined providing the perfect basal rate for each subject that would, given no disturbances, maintain blood glucose concentration at the 110 mg/dl target (average of the euglycemic zone). Further, a perfect bolus should also be provided at the beginning of each meal that does not over or under-compensate for the glucose content of the meal, thus both avoiding late postprandial hypoglycemia and minimizing hyperglycemia prior to returning to the target. On the other hand, the minimum amount of regulation would feasibly still provide the same basal rate but eschew meal disturbance rejection, and thus will be prone to long episodes of hyperglycemia. The performance of each controller is measured using a medically inspired metric that takes into account the three objectives outlined in the control specifications, scored in a linearly scaled approach with the perfect basal-only control scheme serving as the baseline ("0") and the perfect basal-bolus scheme serving as the top performer ("1"). The specific metrics are 1) peak postprandial blood glucose concentrations
2) percent of total time the subject's blood glucose concentration within the euglycemic zone of 80-140 mg/dl;
3) percent of total time the subject's blood glucose concentration spent within the clinically safe non hyper- and hypoglycemic blood glucose zone of 70-180 mg/dl [18]; and
4) percent of total time the subject's blood glucose concentration spent within the hyperglycemic zone of greater than 180 mg/dl.

In addition to these metrics, any controller that causes a subject to experience hypoglycemia b virtue of blood glucose concentrations below 70 mg/dl is discarded.

The controller is turned on after an initialization period of 20 minutes from the beginning of the simulation. A 50 g meal is given at 7 hours after the beginning of the simulation. Each subject's blood glucose profile is recorded for 24 hours after the meal disturbance, with total simulation duration of 31 hours. The controller is activated every 5 minutes, and actual insulin delivery is discretized to the nearest 0.05 U to simulate the limits on current generation subcutaneous insulin pumps [24].

The 1600 and 2400 rules for the correction factor portion of the gain, and the choice between 0.4 and 0.6 rules for the basal scaling factor portion of the gain, are first tested [18].

All tested control schemes and their respective ID to be used in the remaining portion of the results are shown in Table I. $\tau_c$ was fixed at 180 minutes (3 hours). 2400 correction factor rule and 0.4 basal calculation factor is mathematically identical to 1600 and 0.6. Non-personalized versions of the gain based on [14] with and without insulin feedback are also presented for comparison. The average responses of relevant controller variations in FIG. 1 and the scaled performance scores for each controller variation in Table II show that settings of 1600 and 0.4 give the highest scaled scores.

Using these settings, the value for $\tau_c$ is varied as the only tuning parameter from 60 to 300 minutes, in 60 minute intervals. As can be seen in the scaled performance scores in Table II, a $\tau_c$ of 120 minutes gives the best response among the tested settings while still avoiding any instances of hypoglycemia. The controller setting with $\tau_c$ of 1 h was discarded due to the presence of hypoglycemia.

Figure 2:
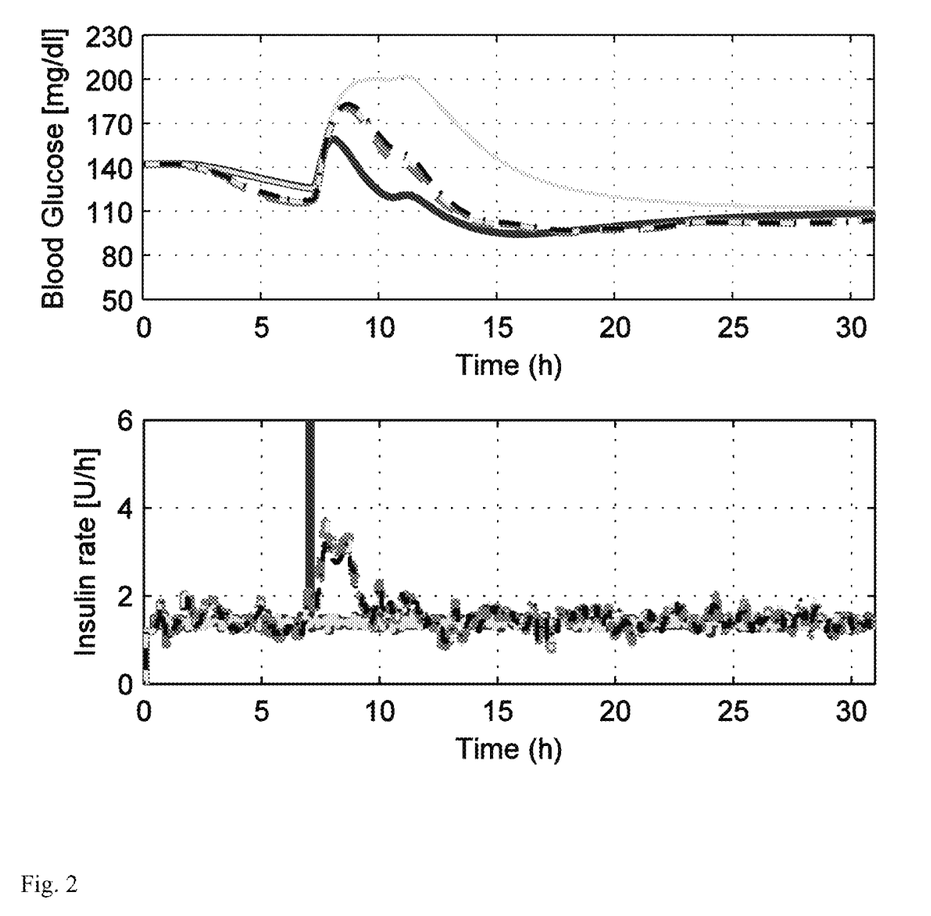
FIG. 2. Comparison of various $\tau_c$ settings with noise.
Figure 3:
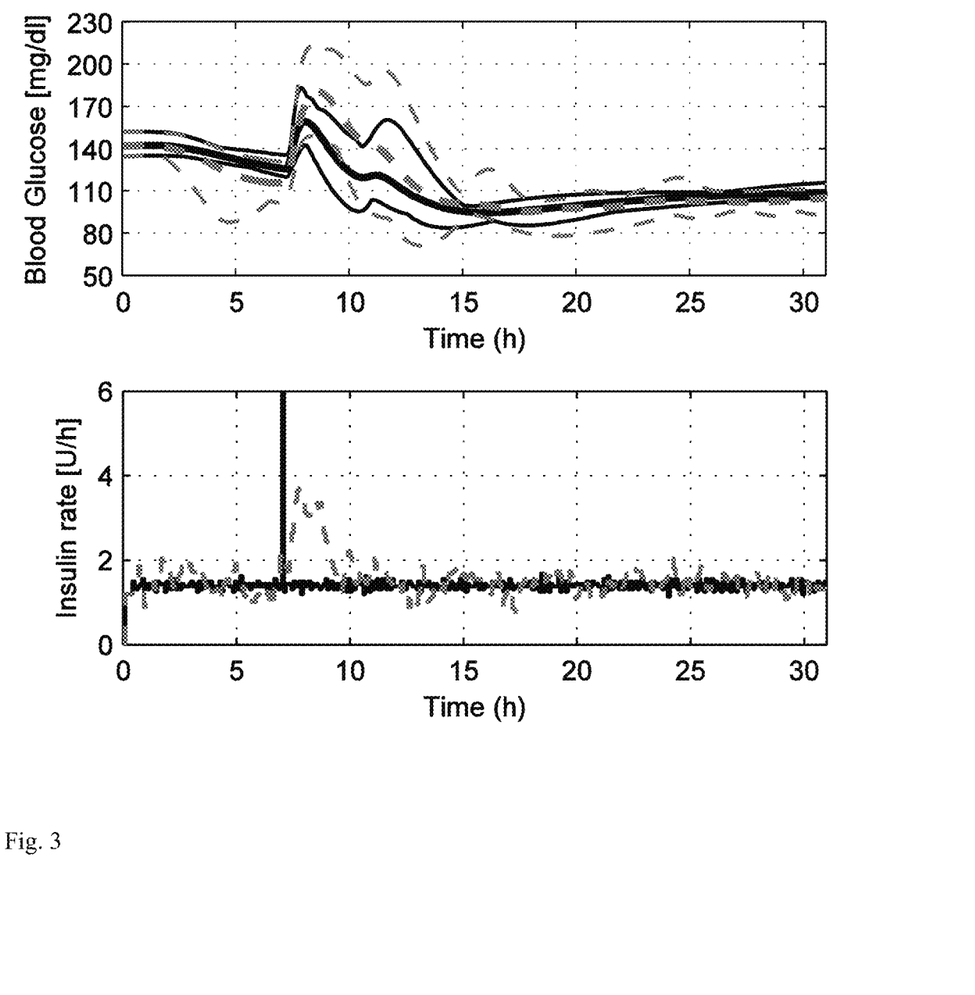
FIG. 3. Comparison of the best PID controller with noise and the optimal basal bolus scheme.

After the optimal IMC PID controller is found through this method under noise-free conditions, the controller is then detuned accordingly within noisy conditions to test for robustness. $\tau_c$ is varied from 2 to 6 hours in 30 minute intervals. $\tau_c$ settings of 4 hours or less induced hypoglycemia. FIG. 2 shows the average glucose and insulin profiles of controllers that does not express hypoglycemia under noisy conditions. As can be in the FIG. 2 and the scaled performance scores in Table II, $\tau_c$ setting of 4.5 h achieves the closest performance to the optimal basal-bolus profile while still avoiding hypoglycemia, with an average postprandial (post meal) peak of 183 mg/dl and over 95 percent of time spent within the safe zone of 70 mg/dl to 180 mg/dl within 24 hours of the meal disturbance. FIG. 3 shows the average, minimum, and maximum values for each step for this setting and is compared with the optimal basal-bolus control scheme. As can be seen in the figure, while the disclosed controller has a slightly higher prandial peak, it still maintains all subject glucose profiles within the target zone for an extreme majority of the simulations and avoids any instances of hypoglycemia.

Discussion

This disclosure demonstrates the value of an IMC-based design method with a personalization scheme to calculate PID controller parameters and combine it with IFB for AP applications. This disclosure also demonstrates the value of the personalization scheme for any MPC controller which is derived from the same model that incorporated the personalization scheme. Under the stated simulation conditions, the subject controller with subject specific personalization of the controller's aggressiveness and inclusion of IFB give good control results based on a set of metrics designed to quantify each controller's adherence to medically inspired objectives. Selection of correct personalization methods and an optimal TC value gives a resulting average subject glucose profile that can closely match the optimal basal-bolus scheme, while avoiding hypoglycemia for all 10 tested subjects.

A 3rd order control-relevant model was used to obtain PID controller parameters through an IMC based approach for AP applications. The resulting PID controller with accompanying IFB scheme was personalized based on a priori subject characteristics and tested on ten simulated subjects under the UVA/Padova metabolic simulator. Optimal controller settings were determined through a set of controller performance metrics, and the PID controller based on the resulting choice in personalization rule parameters and TC was able to achieve comparable performance to the optimal basal-bolus scheme. The average post prandial peak was maintained below 185 mg/dl, and 97% of the combined total simulation time for all subjects was maintained within the target safe blood glucose zone of 70-180 mg/dl with 80% of the time remaining within the euglycemic zone of 80-140 mg/dl all without inducing instances of hypoglycemia. The controller can achieve this performance without a time-consuming model identification step, and thus will have greater utility in practical applications.

An MPC controller was also derived from a $3^{rd}$ order model control-relevant model that incorporates personalization, identical to one used to derive the IMC PID controller. It has been previously shown that an MPC controller can be realized to be identical to a PID controller under appropriate tuning [13]. Thus, the improvements in performance realized by the personalization of the IMC PID controller also directly translate to the improvements in performance that can be realized by the MPC controller derived from an identical model.

FIGURES

Figure 1:
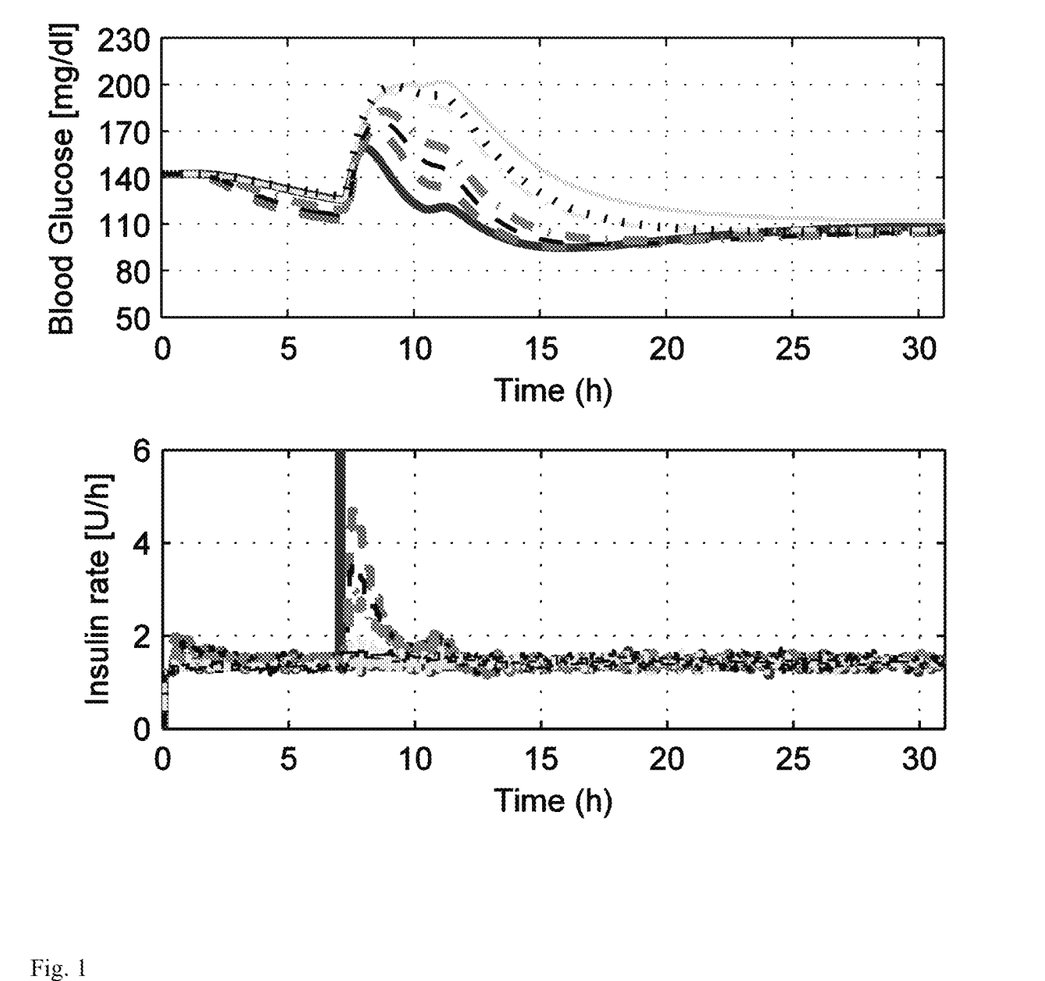
FIG. 1. Comparison of different personalization schemes without noise.

FIG. 1. Comparison of different personalization schemes without noise. Average blood glucose profiles and insulin delivery for 10 in silico subjects simulated in the UVA/Padova metabolic simulator to a 50 g meal disturbance applied to the IMC PID controller as described in the text, with setpoint at 110 mg/dl, $\tau_c$ at 3 h, and various combinations of personalization rule settings as in table I. Solid continuous line represents controller 1 (optimal basal-bolus scheme), thin continuous line represents controller 2 (optimal basal scheme), thick dashed line represents controller 3 (1600 correction factor and 0.4 basal factor), thin dashed line represents controller 4 (1600 correction factor and 0.6 basal factor), thick dash dotted line represents controller 5 (2400 correction factor and 0.6 basal factor), thin dash dotted line represents controller 10 (PID without personalization but with insulin feedback), and thick dotted line represents controller 11 (PID without personalization and without insulin feedback).

FIG. 2. Comparison of various $\tau_c$ settings with noise. Average blood glucose profiles and insulin delivery for 10 in silico subjects simulated in the UVA/Padova metabolic simulator to a 50 g meal disturbance applied to the IMC PID controller as described in the text, with setpoint at 110 mg/dl, correction factor rule chosen as 1600, basal calculation factor chosen as 0.4, and $\tau_c$ varied from 2 h to 6 h in 30 minute intervals. Controller with $\tau_c$ of 4 h or less were discarded due to presence of hypoglycemia. Solid continuous line represents controller 1 (optimal basal-bolus scheme), thin continuous line represents controller 2 (optimal basal scheme), thick dashed line represents controller 17 ($\tau_c$ of 4.5 h), thin dashed line represents controller 18 ($\tau_c$ of 5 h), and thick dash dotted line represents controller 19 ($\tau_c$ of 5.5 h) and thin dash dotted line represents controller 20 ($\tau_c$ of 6 h).

FIG. 3. Comparison of the best PID controller with noise and the optimal basal bolus scheme. Average, minimum, and maximum blood glucose profiles and average insulin delivery for 10 in silico subjects simulated in the UVA/Padova metabolic simulator to a 50 g meal disturbance applied to the IMC PID controller as described in the text, with setpoint at 110 mg/dl, correction factor rule chosen as 1600, basal calculation factor chosen as 0.4, and $\tau_c$ chosen as 4.5 h. Dashed lines represent the controller's average, minimum, and maximum values at each time point and controller insulin delivery profiles. Solid lines represent the same characteristics of the basal bolus scheme.

REFERENCES

[1] "National Diabetes Statistics, 2011," ed: National Institute of Diabetes and Digestive and Kidney Diseases, National Diabetes Information Clearinghouse, National Institutes of Health, 2011.

[2] M. W. Percival, Y. Wang, B. Grosman, E. Dassau, H. Zisser, L. Jovanovič, and F. J. Doyle III, "Development of a multi-parametric model predictive control algorithm for insulin delivery in type 1 diabetes mellitus using clinical parameters," *J. Process Control*, vol. 21, pp. 391-404, 2011.

[3] D. Daneman, "Type 1 diabetes," *Lancet*, vol. 367, pp. 847-58, 2006.

[4] O. Franco, E. Steyerberg, F. Hu, J. Mackenbach, and W. Nusselder, "Associations of Diabetes Mellitus with Total Life Expectancy and Life Expectancy With and Without Cardiovascular Disease," *Arch Intern Med*, vol. 167, pp. 1145-1151, 2007.

[5] G. M. Steil and M. F. Saad, "Automated insulin delivery for type 1 diabetes," *Curr Opin Endocrinol and Diabetes*, vol. 13, pp. 205-211, 2006.

[6] S. A. Weinzimer, G. M. Steil, K. L. Swan, J. Dziura, N. Kurtz, and W. V. Tamborlane, "Fully automated closed-loop insulin delivery versus semiautomated hybrid control in pediatric patients with type 1 diabetes using an artificial pancreas," *Diabetes Care*, vol. 31, pp. 934-9, May 2008.

[7] C. Cobelli, E. Renard and B. Kovatchev, "Artificial pancreas: past, present, future," *Diabetes*, vol. 60, pp. 2672-82, November 2011.

[8] R. S. Parker, F. J. Doyle III and N. A. Peppas, "A model-based algorithm for blood glucose control in type 1 diabetic patients," *IEEE Trans Biomed Eng*, vol. 46, pp. 148-57, February 1999.

[9] R. Hovorka, K. Kumareswaran and J. Harris, "Overnight Closed-Loop Insulin Delivery (Artificial Pancreas) in Adults with Type 1 Diabetes: Crossover Randomized Controlled Studies," *BMJ*, vol. 342, 2011.

[10] E. Dassau, H. Zisser, R. A. Harvey, M. W. Percival, B. Grosman, W. Bevier, E. Atlas, S. Miller, R. Nimri, L. Jovanovic, and F. J. Doyle III, "Clinical Evaluation of a Personalized Artificial Pancreas," *Diabetes Care*, (Accepted For Publication).

[11] E. Atlas, R. Nimri, S. Miller, E. A. Grunberg, and M. Phillip, "MD-logic artificial pancreas system: a pilot study in adults with type 1 diabetes," *Diabetes Care*, vol. 33, pp. 1072-6, May 2010.

[12] H. T. Nguyen, N. Ghevondian and T. W. Jones, "Neural-Network Detection of Hypoglycemic Episodes in Children with Type 1 Diabetes using Physiological Parameters," *Conf Proc IEEE Eng Med Biol Soc*, vol. 1, pp. 6053-6, 2006.

[13] M. W. Percival, H. Zisser, L. Jovanovic, and F. J. Doyle III, "Closed-loop control and advisory mode evaluation of an artificial pancreatic Beta cell: use of proportional-integral-derivative equivalent model-based controllers," *J. Diabetes Sci. Technol.*, vol. 2, pp. 636-44, July 2008.

[14] K. van Heusden, E. Dassau, H. Zisser, D. E. Seborg, and F. J. Doyle III, "Control-Relevant Models for Glucose Control Using A Priori Patient Characteristics," *IEEE Trans Bio Eng*, vol. 59, pp. 1839-1849, 2012.

[15] S. Kanderian and G. M. Steil, "Apparatus and Method for Controlling Insulin Infusion with State Variable Feedback," U.S. Pat. No. 7,806,886, 2007.

[16] G. M. Steil, P. C, N. Kurtz, G. R. Voskanyan, A. Roy, S. Paz, and F. Kandeel, "The Effect of Insulin Feedback on Closed Loop Glucose Control," *J Clin Endocrinol Metab*, vol. 96, pp. 1402-1408, 2011.

[17] B. P. Kovatchev, M. Breton, C. Dalla Man, and C. Cobelli, "In Silico Preclinical Trials: A Proof of Concept in Closed-Loop Control of Type 1 Diabetes," *J. Diabetes Sci. Technol.*, vol. 3, pp. 44-55, 2009.

[18] J. Walsh and R. Roberts, *Pumping Insulin*, 4 ed. San Diego, Calif.: Torrey Pines, 2006.

[19] J. Jaremko and O. Rorstad, "Advances toward the implantable artificial pancreas for treatment of diabetes," *Diabetes Care*, vol. 21, pp. 444-50, March 1998.

[20] D. Bruttomesso, A. Farret, S. Costa, M. C. Marescotti, M. Vettore, A. Avogaro, A. Tiengo, C. Dalla Man, J. Place, A. Facchinetti, S. Guerra, L. Magni, G. De Nicolao, C. Cobelli, E. Renard, and A. Maran, "Closed-loop artificial pancreas using subcutaneous glucose sensing and insulin delivery and a model predictive control algorithm: preliminary studies in Padova and Montpellier," *J. Diabetes Sci. Technol.*, vol. 3, pp. 1014-21, 2009.

[21] "Humalog Highlights of Prescribing Information," E. L. a. Company, Ed., ed. Indianapolis, Ind., 2011, pp. 1-12.

[22] S. Skogestad, "Simple Analytic Rules for Model Reduction and PID Controller Tuning," *Modeling, Identification and Control*, vol. 25, pp. 85-120, 2004.

[23] D. E. Seborg, T. F. Edgar, D. A. Mellichamp, and F. J. Doyle III, *Process Dynamics and Control*, 3rd ed. Hoboken, N.J.: John Wiley & Sons, 2011.

[24] "Paradigm 522 and 722 Insulin Pumps User Guide," ed: Medtronic Minimed, 2008.

TABLE I

CONTROLLER VARIATIONS TESTED

| | | | Personalization Rule Variations | |
| --- | --- | --- | --- | --- |
| Controller ID | Controller Variant | $\tau_e$ (min) | Correction Factor Rule | Basal Calculation Factor |
| 1 | Optimal Basal-Bolus | — | — | — |
| 2 | Optimal Basal | — | — | — |
| 3 | IMC-PID w/feedback | 180 | 1600 | 0.4 |
| 4 | IMC-PID w/feedback | 180 | 1600 (2400 equivalent) | 0.6 (0.4 equivalent) |
| 5 | IMC-PID w/feedback | 180 | 2400 | 0.4 |
| 6 | IMC-PID w/feedback | 60 | 1600 | 0.4 |
| 7 | IMC-PID w/feedback | 120 | 1600 | 0.4 |
| 8 | IMC-PID w/feedback | 240 | 1600 | 0.4 |
| 9 | IMC-PID w/feedback | 300 | 1600 | 0.4 |
| 10 | IMC-PID w/feedback | 180 | — | — |
| 11 | IMC PID w/o feedback | 180 | — | — |
| 12 | IMC-PID w/feedback, noise | 120 | 1600 | 0.4 |
| 13 | IMC-PID w/feedback, noise | 150 | 1600 | 0.4 |
| 14 | IMC-PID w/feedback, noise | 180 | 1600 | 0.4 |
| 15 | IMC-PID w/feedback, noise | 210 | 1600 | 0.4 |
| 16 | IMC-PID w/feedback, noise | 240 | 1600 | 0.4 |
| 17 | IMC-PID w/feedback, noise | 270 | 1600 | 0.4 |
| 18 | IMC-PID w/feedback, noise | 300 | 1600 | 0.4 |
| 19 | IMC-PID w/feedback, noise | 330 | 1600 | 0.4 |
| 20 | IMC-PID w/feedback, noise | 360 | 1600 | 0.4 |

TABLE II

Averaged Performance Metrics and Scaled Metric Values for each Controller with Optimal Balal-Bolus and Optimal Basal Control Schemes as Baseline Performances

| Controller ID | % Time in Hypoglycemia, <70 mg/dl | Peak Blood Glucose [mg/dl] | % above 70-180 mg/dl | % within 70-180 mg/dl | % within 80-140 mg/dl | Scaled Peak Blood Glucose | Scaled % above 70-180 mg/dl | Scaled % within 70-180 mg/dl | Scaled % within 80-140 mg/dl |
| --- | --- | --- | --- | --- | --- | --- | --- | --- | --- |
| 1 | 0 (0) | 209 (25.2) | 13.8 (7.2) | 86.2 (7.2) | 65.8 (9.1) | 0.00 | 0.00 | 0.00 | 0.00 |
| 2 | 0 (0) | 162 (14.4) | 0.11 (0.3) | 99.9 (0.3) | 85.6 (8.9) | 1.00 | 1.00 | 1.00 | 1.00 |
| 3 | 0 (0) | 174 (18.3) | 1.64 (2.6) | 98.4 (2.6) | 83.7 (10.8) | 0.74 | 0.89 | 0.89 | 0.90 |
| 4 | 0 (0) | 181 (19.7) | 3.63 (5.2) | 96.4 (5.2) | 82.1 (8.8) | 0.60 | 0.74 | 0.74 | 0.82 |
| 5 | 0 (0) | 187 (21.2) | 4.62 (6.0) | 95.4 (6.0) | 79.1 (9.7) | 0.46 | 0.67 | 0.67 | 0.67 |
| 6 | 0.70 (2.2) | 167 (16.4) | 1.42 (1.4) | 99 (2.4) | 86 (9.7) | 0.90 | 0.90 | 0.91 | 1.03 |
| 7 | 0 (0) | 170 (17.6) | 0.83 (1.9) | 99.2 (1.9) | 85.2 (11) | 0.82 | 0.95 | 0.95 | 0.98 |
| 8 | 0 (0) | 177 (18.9) | 2.55 (3.5) | 97.5 (3.5) | 82.8 (9.9) | 0.67 | 0.82 | 0.82 | 0.86 |
| 9 | 0 (0) | 180 (19.5) | 3.36 (4.7) | 96.6 (4.7) | 82.4 (8.7) | 0.61 | 0.76 | 0.76 | 0.84 |
| 10 | 0 (0) | 202 (22.8) | 9.95 (6.5) | 80.1 (6.5) | 71.1 (11.7) | 0.15 | 0.28 | 0.45 | 0.27 |
| 11 | 0 (0) | 207 (23.6) | 11.32 (6.8) | 88.7 (6.8) | 68.8 (12.3) | 0.05 | 0.18 | 0.18 | 0.15 |

TABLE II-continued

Averaged Performance Metrics and Scaled Metric Values for each Controller with
Optimal Balal-Bolus and Optimal Basal Control Schemes as Baseline Performances

| Controller ID | % Time in Hypoglycemia, <70 mg/dl | Peak Blood Glucose [mg/dl] | % above 70-180 mg/dl | % within 70-180 mg/dl | % within 80-140 mg/dl | Scaled Peak Blood Glucose | Scaled % above 70-180 mg/dl | Scaled % within 70-180 mg/dl | Scaled % within 80-140 mg/dl |
|---|---|---|---|---|---|---|---|---|---|
| 12 | 1.34 (2.9) | 179 (19.3) | 1.69 (2.4) | 97.0 (4.4) | 80.7 (11.4) | 0.64 | 0.88 | 0.79 | 0.75 |
| 13 | 0.68 (2.1) | 180 (19.4) | 1.96 (2.8) | 97.4 (3.6) | 81.2 (12.0) | 0.62 | 0.86 | 0.81 | 0.78 |
| 14 | 0.48 (1.5) | 181 (19.4) | 2.34 (3.5) | 97.2 (3.8) | 80.9 (11.7) | 0.60 | 0.84 | 0.80 | 0.76 |
| 15 | 0.35 (1.1) | 182 (19.5) | 2.63 (4.1) | 97.0 (4.2) | 80.5 (11.5) | 0.58 | 0.81 | 0.79 | 0.74 |
| 16 | 0.09 (0.3) | 183 (19.6) | 3.20 (4.6) | 96.7 (4.6) | 80.2 (11.0) | 0.56 | 0.77 | 0.77 | 0.73 |
| 17 | 0 (0) | 183 (19.6) | 3.52 (5.1) | 96.5 (5.1) | 79.9 (10.3) | 0.54 | 0.75 | 0.75 | 0.72 |
| 18 | 0 (0) | 184 (19.9) | 3.74 (5.3) | 96.3 (5.3) | 80.1 (9.0) | 0.52 | 0.73 | 0.73 | 0.72 |
| 19 | 0 (0) | 185 (20.1) | 3.87 (5.4) | 96.1 (5.4) | 79.7 (9.1) | 0.50 | 0.72 | 0.72 | 0.70 |
| 20 | 0 (0) | 186 (20.3) | 4.09 (5.5) | 95.9 (5.5) | 79.4 (9.3) | 0.48 | 0.71 | 0.71 | 0.69 |

What is claimed is:

1. An insulin pump controller configured with a model-based personalization scheme for an artificial pancreas (AP) system, the controller comprising a discrete control-relevant model incorporating a priori subject information as design criteria in the model, wherein a scaling factor based on the subject's actual basal insulin value is incorporated in the model to attune the controller's action in cases of model and patient glucose mismatch, wherein the subject's actual basal insulin value is the insulin dose to maintain the subject at euglycemia absent meal disturbances, and an insulin feedback scheme (IFB), which takes into account the amount of insulin previously delivered, accelerating the apparent insulin pharmacokinetics.

2. The controller of claim 1, wherein the controller is a model predictive control (MPC) feedback controller.

3. The controller of claim 2, integrated in an artificial pancreas system further comprising a subcutaneous continuous glucose monitor (CGM) and a continuous subcutaneous insulin injection (CSII) pump to deliver insulin, wherein the continuous glucose monitor provides glucose data to the controller, and the controller directs insulin delivery by the pump.

4. A method comprising directing insulin delivery using the controller of claim 3.

5. The controller of claim 1, wherein the controller is an internal model control (IMC) based design of a proportional-integral-derivative (PID) controller.

6. The controller of claim 5, integrated in an artificial pancreas system further comprising a subcutaneous continuous glucose monitor (CGM) and a continuous subcutaneous insulin injection (CSII) pump to deliver insulin, wherein the continuous glucose monitor provides glucose data to the controller, and the controller directs insulin delivery by the pump.

7. A method comprising directing insulin delivery using the controller of claim 6.

8. The controller of claim 1, wherein a total daily insulin (TDI) clinical parameter is also incorporated to further attune the controller's action.

9. The controller of claim 8, integrated in an artificial pancreas system further comprising a subcutaneous continuous glucose monitor (CGM) and a continuous subcutaneous insulin injection (CSII) pump to deliver insulin, wherein the continuous glucose monitor provides glucose data to the controller, and the controller directs insulin delivery by the pump.

10. A method comprising directing insulin delivery using the controller of claim 9.

11. The controller of claim 1, wherein the controller requires only a single tuning parameter to modify controller performance.

12. The controller of claim 11, integrated in an artificial pancreas system further comprising a subcutaneous continuous glucose monitor (CGM) and a continuous subcutaneous insulin injection (CSII) pump to deliver insulin, wherein the continuous glucose monitor provides glucose data to the controller, and the controller directs insulin delivery by the pump.

13. A method comprising directing insulin delivery using the controller of claim 12.

14. The controller of claim 1, integrated in an artificial pancreas system further comprising a subcutaneous continuous glucose monitor (CGM) and a continuous subcutaneous insulin injection (CSII) pump to deliver insulin, wherein the continuous glucose monitor provides glucose data to the controller, and the controller directs insulin delivery by the pump.

15. A method comprising directing insulin delivery using the controller of claim 14.

* * * * *